United States Patent [19]

Waskovsky

[11] Patent Number: 4,918,018

[45] Date of Patent: Apr. 17, 1990

[54] MICROORGANISM FOR USE IN INDUSTRIAL PROCESSES

[75] Inventor: James Waskovsky, Socorro, N. Mex.

[73] Assignee: Chemolithotrophs, Inc, Socorro, N. Mex.

[21] Appl. No.: 131,425

[22] Filed: Dec. 10, 1987

[51] Int. Cl.$^4$ .......................... C12N 1/20; C12R 1/01
[52] U.S. Cl. .................................. 453/252.1; 435/822
[58] Field of Search ............... 435/262, 264, 282, 252, 435/822, 263; 75/101 R, 117; 423/27

[56] References Cited

U.S. PATENT DOCUMENTS

| | | | |
|---|---|---|---|
| 3,305,353 | 2/1967 | Duncan et al. | 75/101 |
| 3,856,913 | 12/1974 | McElroy et al. | 423/27 |
| 4,376,826 | 3/1983 | Mynatt | 435/253 |
| 4,483,923 | 11/1984 | Blair | 435/253 |
| 4,571,387 | 2/1986 | Bruynesteyn et al. | 435/262 |
| 4,572,898 | 2/1986 | Zeikus | 435/200 |

OTHER PUBLICATIONS

Olsen, T., "Desulfurization of an Ohio Coal by Microbiological Leaching", New Mexico Institute of Mining and Technology, Socorro, New Mexico, May, 1980.

Ashman, P., "Microbiological Desulfurization of a New Mexico Coal", New Mexico Institute of Mining and Technology, Socorro, New Mexico, Apr. 1980.

Mehta, A., "Fundamental Studies on the Contributions of Galvanic Interactions to the Acid–Bacteria Leaching of Mixed Metal Sulfides", New Mexico Institute of Mining & Technology, Socorro, NM, Aug. 1981.

Microbes as Metal Traps, pp. 153–159.

Primary Examiner—Thomas G. Wiseman
Assistant Examiner—Richard C. Peet
Attorney, Agent, or Firm—Fleit, Jacobson, Cohn, Price, Holman & Stern

[57] ABSTRACT

A purified culture of *Ferroxifunis bagdadii* capable of extracting metals from mining heaps, liquefying and desulfurizing coal, and decolorizing textile mill wastewaters.

1 Claim, 2 Drawing Sheets

MICROORGANISM FOR USE IN INDUSTRIAL PROCESSES

BACKGROUND OF THE INVENTION

1. Field of the Invention

This invention relates to a novel microorganism, *Ferroxifunis bagdadii*, and its isolation and purification from a natural source. This invention also relates to industrial processes utilizing a pure culture of *Ferroxifunis bagdadii*, including the bioextraction of mining ores and tailings, the degradation of textile plant wastewater pollutants into innocuous materials compatible with the environment, and the liquefaction and desulfurization of coal.

2. Brief Description of the Prior Art

Bioextraction Of Mining Ores: Microorganisms have been used to leach ores from mine waters for about thirty years. The basic reaction mediated by microorganisms is:

$$4FeSO_4 + 2H_2SO_4 + O_2 \text{ (electron receptor)} \rightarrow 2Fe_2(SO_4)_3 + 2H_2O.$$

Ferric iron is required to oxidize the sulfide in the minerals, thereby releasing copper into the acidified solution. *Thiobacillus ferroxidans* is one microorganism with known utility in this regard. *T. ferroxidans* exhibits an iron oxidation rate of 40–50 mg/l/hour for $10^6$ bacteria/$cm^3$. However, there are many characteristics of Thiobacillus which limit its bioextractive utility. Among other things, Thiobacilli exhibit a slow growth rate and are intolerant of light, arsenic, chlorides, high copper content, high temperatures, lack of oxygen, and high molybdenum concentrations. Attempts to overcome the growth rate problem and increase the iron oxidation rate observed with Thiobacillus have included the addition of silver to the effluent, which increases the iron oxidation rate to 360 mg/l/hour.

Degradation Of Textile Plant Wastewater Pollutants: Inherent in the manufacturing of textiles is the production of wastewater containing organic and inorganic materials which render the wastewater unsuitable for reuse and/or release into the biosphere.

Known processes for degrading textile plant wastewater pollutants have incorporated the utilization of microorganisms such as Thiobacillus. However, such organisms do not survive well in industrial effluents containing starches, formaldehydes and alcohols, thus limiting their utility in degrading wastewater pollutants.

Desulfurization Of Coal: In recent years, the problem of "acid rain" has become well-known. The problem originates in the burning of coal to which sulfur is bound. Upon combustion, sulfur dioxide ($SO_2$) is released into the atmosphere where it will combine with rain water to form sulfuric acid, hence, the term "acid rain." Present methods of dealing with the problem of desulfurizing coal have included the utilization of microorganisms such as Thiobacillus thioparus. However, the slow growth of Thiobacillus requires several weeks residence time in the bioreactor. In addition, Thiobacillus requires aerobic, acidophillic and autotrophic conditions for growth.

SUMMARY OF THE INVENTION

Accordingly, it is an object of this invention to provide a biological process for the extraction of metal ores from dump ores or mine tailings utilizing a microorganism which grows well and exhibits a high iron oxidation rate in mine effluent. A further object of this invention is to provide a biological process for the extraction of metal ores utilizing a culture of the microorganism *Ferroxifunis bagdadii*.

Another object of this invention is to provide a biological process for the treatment of textile mill wastewater effluent utilizing a microorganism which can survive in wastewater containing products such as starches, formaldehydes, and alcohols; can turn pollutants into innocuous materials compatible with the environment; and, which, because of its sulfur oxidizing abilities, can oxidize diazo dyes to the standards of the Environmental Protection Agency (EPA). A further object of this invention is to provide a process for the biological degradation of textile plant wastewater pollutants utilizing a pure culture of the microorganism *Ferroxifunis bagdadii*.

Yet another object of this invention is to provide a biological process for desulfurizing coal, prior to combustion, utilizing a microorganism that grows quickly enough to limit residence time in bioreactors to a matter of days and whose growth is not dependent on the presence of aerobic, acidophilic, mesophilic, and autotrophic conditions. A further object of this invention is to provide a process for desulfurizing coal, prior to combustion, utilizing a pure culture of *Ferroxifunis bagdadii*.

An additional object of this invention is to provide a pure culture of *Ferroxifunis bagdadii*.

In one embodiment, this invention provides a process for the extraction of metal ores from dump ores or mine tailings, which comprises treating effluent and/or mine heaps with a pure culture of the microorganism *Ferroxifunis bagdadii*.

In another embodiment, this invention provides a process for degrading textile mill wastewater which comprises treating wastewater effluent from a textile mill with a pure culture of the microorganism *Ferroxifunis bagdadii*.

In another embodiment, this invention provides a process for desulfurizing coal, prior to combustion, which comprises innoculating coal with a pure culture of the microorganism *Ferroxifunis bagdadii*.

In yet another embodiment, this invention provides a pure culture of the microorganism *Ferroxifunis bagdadii*, having the characteristics described below.

DETAILED DESCRIPTION OF THE INVENTION

Figure 1:
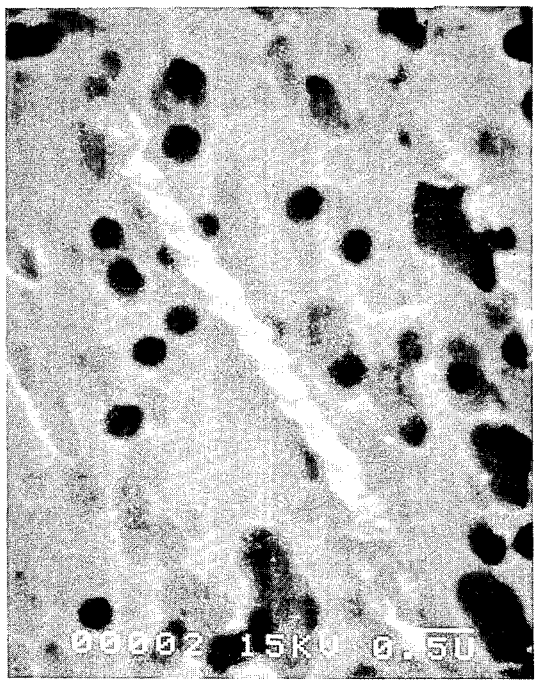

The microorganism *Ferroxifunis bagdadii* was isolated from acid mine effluent at the Cyprus Bagdad Company located in Bagdad Arizona.

The pure culture was isolated from 200 cc undiluted mine effluent to which various supplements were added. After incubation at 37° C. for four days, a rusty coloration was observed in the effluent to which had been added: 0.1 gram ascorbic acid, 0.1 g $MgSO_4\,7H_2O$, 0.02g Na-molybdenate, and 5.6 grams $FeSO_4$; henceforth, referred to as the isolating medium.

Ten milliliter aliquouts of isolating medium were then added to 100 milliliters of solutions containing arsenic (5 ml. of 1.5% arsenic trioxide solution), copper (5 g/l $CuSO_4$), molybdenum (0.3 g/l sodium molybdenate), 5 ml concentrated xylene, zinc (5 g/l $ZnSO_4$). The basic solution contained 0.4 g/l $K_2HPO_4$, 0.4 g/l $(NH_4)_2SO_4$, and 0.4 g/l $MgSO_4\,7H_2O$. All solutions were incubated at 37° C. Growth, as judged by turbidity, was observed within 72 hours. Further purification was carried out with an inoculant from the copper-containing solution.

A 5 ml. inoculant from the copper-containing solution was placed in 100 ml. of the basic solution described above which additionally contained either 10, 20, or 30 g/l $CuSO_4$. All solutions were incubated at 37° C. Growth, as judged by turbidity, was noted within four days, in tubes containing 10 and 20 g/l $CuSO_4$. No growth was observed in the solution containing 30 g/l $CuSO_4$.

For further purification, inocula were taken from the solution containing 20 g/l $CuSO_4$ and streaked, with a wire loop, on solid agar-agar media containing basal salts (0.4 g $K_2HPO_4$, 0.4 g $(NH_4)_2SO_4$ and 0.4 g $MgSO_4$ $7H_2O$), and 10, 20 or 30 g/l $CuSO_4$.

Distinct colonies were observed after four days incubation at 37° C. and the addition of gram stain revealed the presence of gram negative rods. An isolated colony from the plate containing 20 g/l $CuSO_4$ was streaked onto a similar plate. Colony growth was observed after six days incubation at 37° C. Again, the addition of gram stain revealed the presence of gram negative rods. The procedure was repeated three times to obtain pure colonies. Purity was confirmed with scanning electron microscopy.

Pure cultures were maintained in liquid feedstock containing 0.4 g/l $K_2HPO_4$, 0.4 g/l $(NH_4)_2SO_4$, 0.4 g/l $MgSO_4$ $7H_2O$, 27.8 g/l $FeSO_4$ $7H_2O$, and 10 ml. Bagdad mine effluent. Pure cultures were also maintained on slants containing an agar-agar/basal salt solid medium prepared as follows: Basal salts (0.4 g $(NH_4)_2SO_4$, 0.4 g $MgSO_4$ $7H_2O$, 0.4 g $K_2HPO_4$) were added to 500 ml distilled water. This solution was acidified with concentrated sulfuric acid to pH 2.1. In a second flask, 12 grams agar-agar was added to 500 ml distilled water. Both flasks were subjected to 15 PSI at 126° C. for 20 minutes. After cooling to 40° C., the contents of both flasks were combined in a third flask to which was added 27.8 g $FeSO_4$.

The pure *Ferroxifunis bagdadii* is a weakly gram negative, non-spore forming, double stranded rope-like organism with a possible polar appendage. FIG. 1 is an electron micrograph showing the double stranded, rope-like appearance of the Ferroxifunis at 18,000 magnification. The cells are about 4 microns in length and 0.25 microns in width and are free swimmers. *Ferroxifunis bagdadii* is a facultative anaerobe, exhibiting good growth in a $CO_2$ enriched environment. The cells form large spreading colonies on heterotrophic media. No vitamin supplements are required for growth. No odor is given off by cultures of *Ferroxifunis bagdadii* on inorganic media while a pungent odor is given off by cultures on nutrient broth. With the passage of growth time on organic media, *Ferroxifunis bagdadii* forms a pellical on the surface of a narrow mouth tube.

*Ferroxifunis bagdadii* forms transparent, concave, pinpoint colonies with a smooth edge on solid media containing silver and copper. Brown-orange encrustations are observed when growth occurs on iron media. Growth in the presence of aluminum, iron or ammonium leads to the formation of jarosite. Peach fuzz growth is observed on media containing basal salts.

Figure 2:
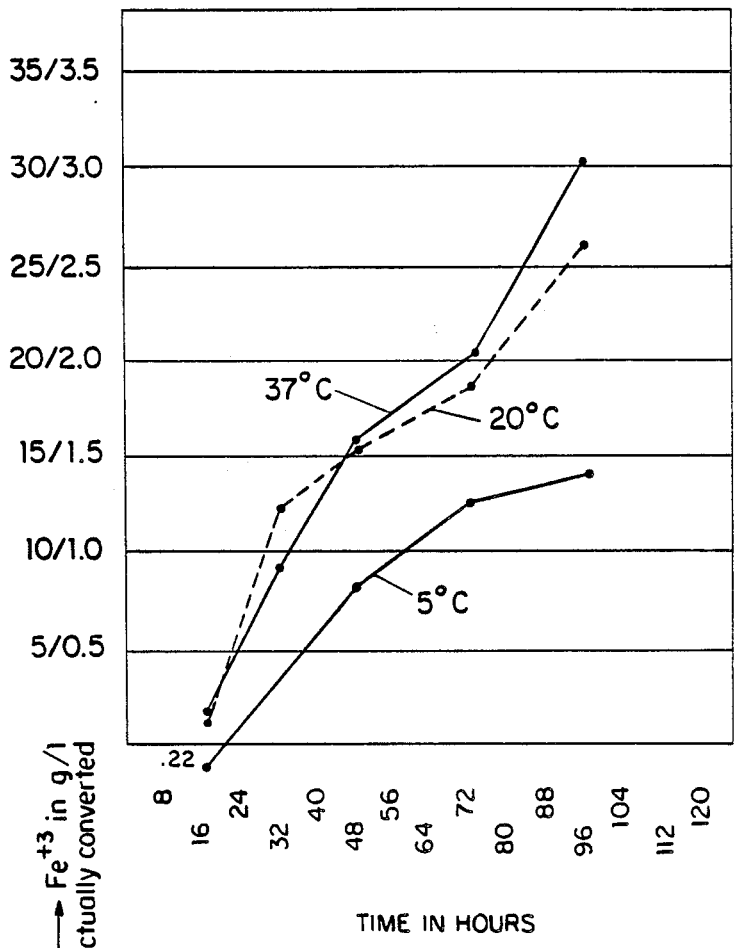

*Ferroxifunis bagdadii* is very tolerant of heavy metals, such as arsenic, copper, antimony, silver, uranium, iron, and molybdenum. The microorganism is a strong iron oxidizer. Iron oxidation rates in excess of 900 mg/l/hour have been observed in straight mine effluent. The ferrous iron content of copper mine effluents vary but even at iron concentrations of 28 g/l, Ferroxifunis oxidizes ferrous iron to ferric iron. The pH of copper mine effluents typically runs between 1.5 and 3.0 and Ferroxifunis will oxidize iron in this range. The microorganism will also oxidize iron over a wide range of temperatures, as shown in FIG. 2. At 5° C., an iron oxidation rate of 600 mg/l/hour is observed; at 37° C., 1000 mg/l/hour.

*Ferroxifunis bagdadii* can also derive energy from the oxidation of sulfur, sulfide, sulfite, thiosulfates, polythionates, antimony and carbon. Furthermore, the microorganism grows well in toxic solutions (1 g/l) of thioacetamide.

*Ferroxifunis bagdadii* is also capable of decolorizing textile wastewater. Unlike other microorganisms used for this purpose, Ferroxifunis does not require constant pH monitoring, a continuous food supply, or a large amount of substrate to maintain activity. In addition, Ferroxifunis is not easily shocked by large loadings. Furthermore, Ferroxifunis survives well in industrial solvents such as formaldehydes and alcohols.

A suitable growth temperature range for *Ferroxifunis bagdadii* is about 5° to 40° C., with optimal growth occurring at 37° C. The microorganism is also thermoduric, surviving at temperatures as high as 80° C. A suitable pH range is 1.7 to 9.4, with optimal growth occurring at pH 2.1.on inorganic media and at pH 3.8 on organic media.

On the basis of the morphological, cultural, and physiological characteristics set forth above, it has been determined that this microorganism is a new species, designated as *Ferroxifunis bagdadii*. A culture of this strain has been deposited in the American Type Culture Collection and has received an accession number, ATCC-53601.

The microorganism *Ferroxifunis bagdadii* can be employed alone or in combination with other microorganisms conventionally used in the described industrial processes. This invention also includes the use of any variants of *Ferroxifunis bagdadii*, either alone, or in combination with other conventionally used microorganisms.

In order to further demonstrate the effectiveness of the pure culture of *Ferroxifunis bagdadii*, the following examples are given as exemplary of the invention but without intending to limit the invention to these examples.

EXAMPLE 1 - BIOEXTRACTION OF ORES

Experimentation was performed to release copper from chalcopyrite, $CuFeS_2$ according to the following reaction mediated by *Ferroxifunis bagdadii*:

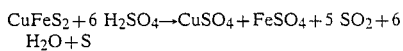

$$CuFeS_2 + 6\ H_2SO_4 \rightarrow CuSO_4 + FeSO_4 + 5\ SO_2 + 6\ H_2O + S$$

Chalcopyrite (1500 grams) was washed in tap water and placed in a one gallon jar. Basal salts (0.75 g/l $MgSO_4$, 0.75 g/l $K_2HPO_4$, 0.75 g/l $(NH_4)_2SO_4$) and 1500 ml distilled water were added to the jar. The contents of the jar were acidified to pH 2.2 with concentrated sulfuric acid. The mixture was shaken and then inoculated with 5cc purified *Ferroxifunis bagdadii* in feedstock medium, containing $10^6$ microorganisms. A control vessel, lacking the microorganism, was also established. The jars were incubated at 37° C., without shaking. Samples were collected every six days for the detection of free copper via the addition of ammonium hydroxide. The presence of free copper was indicated by a color change from clear to blue. Free copper was detected after 36 months in chalcopyrite leach liquor from the inoculated ore. Passivation was observed in the non-inoculated ore after 19 months, with no free copper detected.

EXAMPLE 2 - TREATMENT OF TEXTILE WASTEWATER

Experimentation was performed to demonstrate that *Ferroxifunis bagdadii* decolorizes the diazo dyes found in textile mill wastewaters. Purified *Ferroxifunis bagdadii* (2 ml feedstock) was added to 2 liters of distilled water containing 25 grams glutamic acid and 25 grams glucose. The pH of the solution was 3.8. After six days of microbial growth, dye waste effluent from the Oxford Textile firm in Oxford, New Jersey was added to the solution. All color was removed within three days.

EXAMPLE 3 - DESULFURIZATION OF COAL

Experimentation was performed to demonstrate the effectiveness of Ferroxifunis in desulfurizing coal.

Coal of U.S. Standard Sieve -60 mesh, containing 2.8% sulfur was added to 3 liters distilled water. This 14% coal slurry was acidified with concentrated sulfuric acid to a pH of 4.2. Basal salts 1.5 g $MgSO_4$, 1.5 g $(NH_4)_2SO_4$, 1.5 g $K_2HPO_4$) and sucrose (15 grams) were added to the acidified coal slurry. This slurry was then added to a bioreactor. A pump was used to create fine bubbling on the surface for aeration. At time 0, 50 ml of slurry was removed for sulfate determination via known methods. The slurry was then inoculated with 20 cc purified *Ferroxifunis bagdadii* in feedstock and incubated at 37° C. At various sampling times, 50 ml aliquots of slurry were removed and treated with 0.2 ml of 2% glutaraldehyde to stop microbial oxidation. These samples were stored at 5° C. until sulfate determinations were conducted. At day four, oxidation rates of 850 mg/l/hour were observed.

What is claimed is:

1. A substantially pure culture of *Ferroxifunis bagdadii*, having the identifying characteristics of ATCC 53601.

* * * * *